(12) United States Patent
Tsai et al.

(10) Patent No.: US 7,298,476 B2
(45) Date of Patent: Nov. 20, 2007

(54) METHOD AND SYSTEM FOR FAR-FIELD MICROSCOPY TO EXCEEDING DIFFRACTION-LIMIT RESOLUTION

(75) Inventors: Hai-Lung Tsai, Rolla, MO (US); Ya Cheng, Rolla, MO (US)

(73) Assignee: Laser Microtech, L.L.C., Rolla, MO (US)

( * ) Notice: Subject to any disclaimer, the term of this patent is extended or adjusted under 35 U.S.C. 154(b) by 273 days.

(21) Appl. No.: 11/251,017

(22) Filed: Oct. 14, 2005

(65) Prior Publication Data

US 2007/0096038 A1    May 3, 2007

(51) Int. Cl.
*G01N 21/64* (2006.01)
(52) U.S. Cl. .................... 356/318; 356/417; 250/458.1
(58) Field of Classification Search ................ 356/317, 356/318, 417; 250/458.1, 459.1, 461.1
See application file for complete search history.

(56) References Cited

OTHER PUBLICATIONS

Elangovan et al. Bleed-through and Photobleaching Correction in Multi-photon FRET Microscopy, Proceedings of SPIE, vol. 4262, 2001, pp.177-185.*

* cited by examiner

*Primary Examiner*—F. L. Evans
(74) *Attorney, Agent, or Firm*—Roger Chu

(57) ABSTRACT

The bio-sample (e.g., a live cell) is labeled with a proper number of nanoparticles. Each nanoparticle is pre-co-doped with a controlled ratio of fluorophore donors and acceptors. Two laser pulses are applied to the bio-sample. The first laser pulse has a center wavelength near the peak of absorption spectrum of acceptors. The intensity of first laser pulse is adjusted such that FRET saturation occurs near the center of the focal spot. The focal spot of the first laser pulse is a diffraction-limited Airy disk that has the highest laser intensity in the center of the focal spot. The second laser has a center wavelength in the emission spectrum of acceptors and with a uniform intensity distribution throughout the focal spot. The fluorescence emission from acceptors after two laser pulses is from an area that is smaller than the diffraction-limited focal spot. Hence, a higher than diffraction-limit resolution is achieved.

34 Claims, 13 Drawing Sheets

METHOD AND SYSTEM FOR FAR-FIELD MICROSCOPY TO EXCEEDING DIFFRACTION-LIMIT RESOLUTION

BACKGROUND OF THE INVENTION

1. Field of the Invention

The present invention generally relates to the field of microscopy and more particularly to techniques for exceeding diffraction-limit resolution in far-field microscopy by using nanoparticles co-doped with donor-acceptor dyes, laser pulses, and the method of fluorescence-resonance-energy-transfer-induced-emission-depletion (FRET-IED).

2. Description of the Related Art

The advancement in biological research has progressed very rapidly in the last couple of decades. One of the important tools helping this progress is microscopy that is used to obtain an enlarged view of an object so that it is possible to observe details that otherwise could not be observed. In order to view the precise location and the nature of the interactions between, for example, specific molecular species in live cells, a conventional far-field optical laser scanning microscope (LSM) has been used. LSM is used to observe tiny objects until it reaches a well-known limitation defined by Rayleigh criterion, which is also known as "diffraction-limit" is reached. As the light (i.e., laser) wavelength normally used in LSM is greater than about 400 nanometers (nm), the diffraction limit is approximately equal to 200 nm which is about one-half of the wavelength. Light waves emitted from a point source cannot be focused onto an infinite small spot by the objective lens of a microscope and, as a result, cannot distinguish two points at a distance less than the diffraction limit. Today, a microscope capable of resolution finer than 200 nm is needed in many biological research areas.

The electron microscope and short wavelengths (e.g., the X-ray) microscopes can achieve resolution less than 200 nm employing, respectively, electrons and X-ray as the scanning source. These sources have much shorter wavelengths as compared to normal laser light and, hence, carry high energies that can kill live cells during scanning. This defeats the purpose of observing live cells and thus is not a solution.

Another approach used to overcome the diffraction limit is the scanning near-field optical microscopy (SNOM). In SNOM, the light can be confined to a smaller size than the focal spot of the diffraction limit using a small aperture right above the object. However, this technique can only work within a very short decay distance from the small aperture due to the nature of the evanescent wave. As a result, SNOM is only good to scan the surface of the object. Similarly, an atomic force microscope (AFM), which can achieve a few nanometers of resolution, is limited to the observation of the object's surface. In other words, both SNOM and AFM are unable to achieve the desired three-dimensional images of, for example, live cells.

As a result, there is a need for breaking the diffraction limit using a conventional optical far-field microscope with one objective lens to observe live cells.

SUMMARY OF THE INVENTION

The purpose of this section is to summarize some aspects of the present invention and to briefly introduce some preferred embodiments. Simplifications or omissions may be made to avoid obscuring the purpose of the section. Such simplifications or omissions are not intended to limit the scope of the present invention.

The present invention pertains to method and system of breaking the diffraction limit in conventional laser scanning microscopy. According to one aspect, a plurality of transparent nanoparticles (e.g., silica) is co-doped with donor dyes and acceptor dyes with a controlled ratio (e.g., 5:1). After the donor is excited by an energy source such as a laser pulse, the fluorescence resonance energy transfer (FRET) will occur between the donor-acceptor pair, if these donor-acceptor fluorophores are located within the Förster distance. Choosing a proper size of nanoparticle (e.g., silica nanoparticle with a diameter of 2.5 nm), in accordance with the Förster theory, guarantees a FRET process will occur between the donors and the acceptors that have been co-doped onto a nanoparticle. The co-doped nanoparticles are used to label the sample or object (e.g., a live cell with three dimensional structure) of interest. The sample is then placed in a three-dimensional (3D) motion stage controlled by a computer. The sample is then scanned under the objective lens of the laser scanning microscope. The software module controls the 3D motion stage to ensure that the entire sample is laser scanned in a trajectory to produce a 3D image. A set of three dichroic mirrors and a filter are set up to properly reflect and transmit two laser pulses to be used in the laser scanning process and the fluorescence emitted from the acceptors. The wavelength of the first laser pulse is generally chosen to be near the peak value of the acceptor's absorption spectrum. The intensity of the first laser pulse is carefully determined to ensure a desired number of donors are excited. A highest possible numerical aperture of optics is used for the first laser pulse to ensure that the focal spot size is as small as possible and near the diffraction limit of the light. After the first laser pulse excitation is completed, the first FRET process will occur immediately between the excited donors and the acceptors. The laser intensity profile at the focal spot of the first pulse has an Airy pattern with the maximum intensity at the center. Hence, more donors will be excited for the nanoparticles near the central area of the laser focal spot as compared to those near the edge of the laser focal spot. Because the ratio of donors and acceptors co-doped onto a nanoparticle is pre-determined, the number of excited donors at the focal spot of the first laser pulse is controlled with the intensity of the first laser pulse in such a way that the number of excited donors is slightly more than that of the acceptors on a nanoparticle which is located in the central area (i.e., an inner circular area) of the focal spot. As a result, the first FRET process is saturated in the central area (i.e., an inner circular area) of the focal spot. In other words, for nanoparticles near the central area of the focal spot, there are still excited donors existed not yet transferring their energy to acceptors during the first FRET process.

A second laser pulse is then applied to accelerate the energy depletion of the excited acceptors as a result of the first FRET process. The center wavelength of the second laser pulse is set to the extreme value of the acceptor's emission spectrum; thereby the second laser pulse is configured to deplete the energy of the excited acceptors and not to excite donors. The duration of the second laser pulse is set to a value that is significantly shorter than the FRET lifetime between the donors and the acceptors. For example, if the duration of the second laser pulse is set to 60 picoseconds (ps), while the FRET lifetime is 30 ps, then during the first 30 ps, the energy of excited acceptors due to the first FRET process is depleted. And, in the next 30 ps, as the first FRET process still continues, more excited donors continue to transfer their energy to acceptors. As the second laser pulse is still on, all of the exited donors and acceptors will be depleted. So, if the duration of the second pulse is longer than the FRET lifetime of a donor-acceptor pair, there will be no fluorescence emission from acceptors to be detected. Hence, the saturation of the second laser pulse should be significantly shorter than the FRET lifetime. Immediately after the second laser pulse, some of the excited donors in nanoparticles near the central area (i.e., inner circular area) at the focal spot of the first laser pulse remain, while all of the acceptors have returned to their ground state (i.e., depleted). The fluorescence emission from acceptors due to a second FRET process can be detected and recorded. But, if the duration of the second laser pulse is too short, the spectrum width of the second laser pulse will be too wide to be distinguishable from the fluorescence emission from acceptors. Therefore, the spectrum width of the second laser pulse should be chosen such that a proper filter can be used to effectively block out the second laser pulse with little or no loss of the fluorescence emission from acceptors. The second laser pulse should also have a uniform laser intensity distribution throughout the focal spot of the first laser pulse. In order to achieve uniform intensity, the numerical aperture of the objective lens for the second laser pulse is smaller than that for the first laser pulse. After the two laser pulses have applied to a particular point of interest on the sample, a second FRET process will occur between the remaining excited donors and depleted acceptors. The fluorescence emitted from acceptors due to the second FRET process is detected and recorded by a photomultiple tube (PMT) controlled by the computer. A 3D image of the sample is created by repeating the scanning for every point of interest of the 3D sample. Because the remaining excited donors for the second FRET are only located in the inner circular area of the diffraction-limited focal spot of the first laser pulse, the diffraction limit is broken. In other words, the fluorescence emitted from the second FRET is from a circular area with a diameter smaller than the diffraction limit. The actual area (i.e., resolution) can be determined and is controlled by several parameters, including, but not limited to, the characteristics of donors and acceptors, the ratio of the number of the donor and the acceptor, the laser intensity of the first laser pulse.

Other objects, features, and advantages of the present invention will become apparent upon examining the following detailed description of an embodiment thereof, taken in conjunction with the attached drawings.

BRIEF DESCRIPTION OF THE DRAWINGS

These and other features, aspects, and advantages of the present invention will be better understood with regard to the following description, appended claims, and accompanying drawings as follows:

DETAILED DESCRIPTIONS OF THE PREFERRED EMBODIMENTS

Figure 1A:
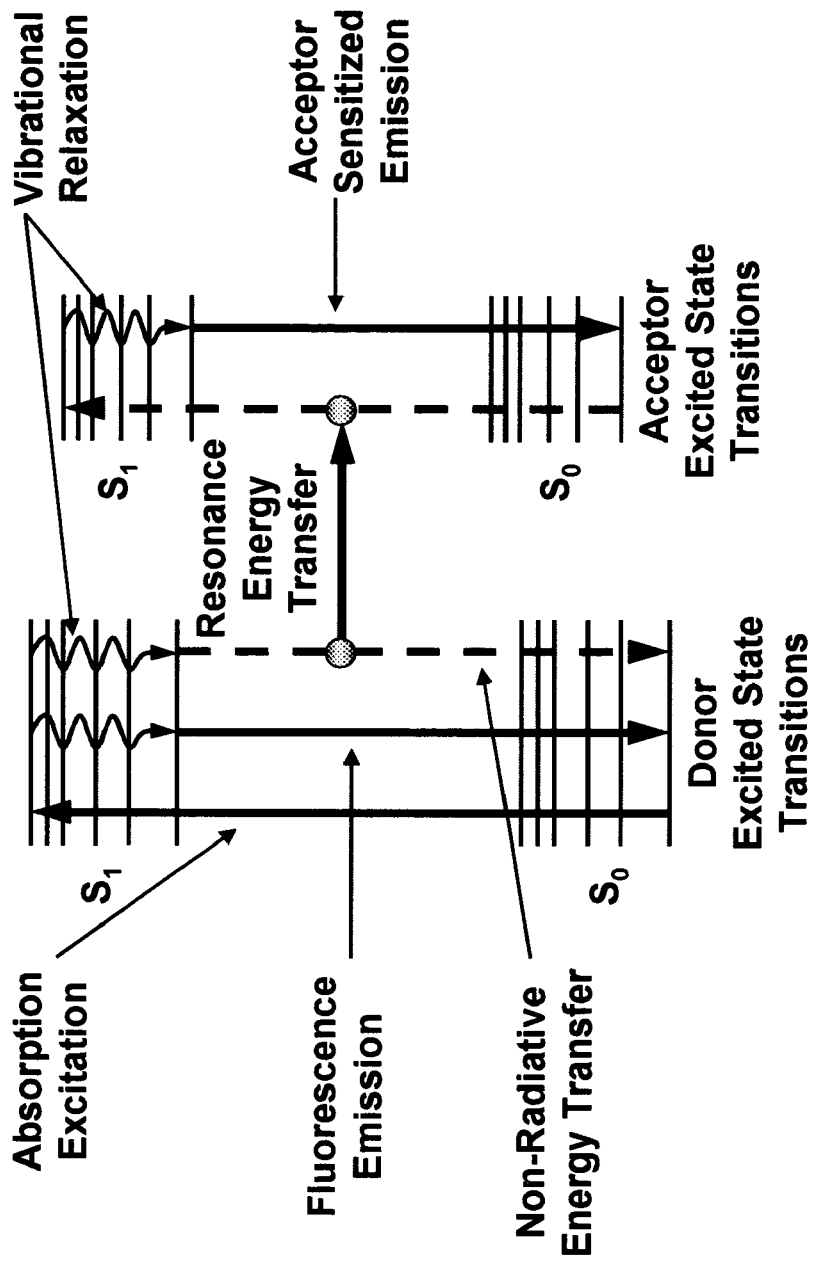
FIG. 1A shows the resonance energy transfer Jablorski diagram.

The present invention discloses the method and system as it pertains to exceeding diffraction-limit resolution in laser scanning fluorescence microscopy using fluorescence-resonance-energy-transfer-induced-emission-depletion (FRET-IED) technique. According to one aspect, the present invention applies two laser pulses to induce FRET-IED between controlled concentrations of donors and acceptors co-doped on a nanoparticle. As a result of this technique, the fluorescence emission from the acceptors is within a circular area smaller than that of the diffraction-limited focal spot.

In the following description, numerous specific details are set forth in order to provide a thorough understanding of the present invention. However, it will become obvious to those skilled in the art that the present invention may be practiced without these specific details. The descriptions and representations herein are the common means used by those experienced or skilled in the art to most effectively convey the substance of their work to others skilled in the art. In other instances, well-known components have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments.

To facilitate the description of the present invention, it deems necessary to provide definitions for some terms that will be used throughout the disclosure herein. It should be noted that the definitions following are to facilitate the understanding and describe the present invention according to an embodiment. The definitions may appear to include some limitations with respect to the embodiment, the actual meaning of the terms has applicability well beyond such embodiment, which can be appreciated by those skilled in the art:

nm—nanometer ($10^{-9}$ meter).
ns—nanosecond ($10^{-9}$ second).
ps—picosecond ($10^{-12}$ second).
fs—femtosecond ($10^{-15}$ second).

Fluorescence microscopy—Typical fluorescence microscopy techniques rely upon the absorption by a fluorophore of light at one wavelength (excitation), followed by the subsequent emission of secondary fluorescence at a longer wavelength. The excitation and emission wavelengths are often different and separated from each other by tens to hundreds of nanometers.

Nanoparticle is referred to as a particle with a diameter between 1 nm and 100 nm.

FRET stands for fluorescence resonance energy transfer. The mechanism of fluorescence resonance energy transfer involves a donor fluorophore in an excited electronic state, which may transfer its excitation energy to a nearby acceptor chromophore in a non-radiative fashion through long-range dipole-dipole interactions. The theory supporting the energy transfer is based on the concept of treating an excited fluorophore as an oscillating dipole that can undergo an energy exchange with a second dipole having a similar resonance frequency. In this regard, resonance energy transfer is analogous to the behavior of coupled oscillators, such as a pair of tuning forks vibrating at the same frequency. In contrast, radiative energy transfer requires emission and re-absorption of photons and depends on the physical dimensions and optical properties of the specimen, etc. Unlike radiative mechanisms, the resonance energy transfer can yield a significant amount of structural information concerning the donor-acceptor pair.

FRET lifetime is defined as the donor's fluorescence lifetime in the presence of the acceptor.

Presented in FIG. 1A is a Jablonski diagram 100 illustrating the coupled transitions involved between the donor emission and the acceptor absorbance in FRET. Absorption and emission transitions are represented by straight vertical arrows (upward and downward, respectively), while vibrational relaxation is indicated by wavy arrows. The coupled transitions are drawn with dashed lines that suggest their correct placement in the Jablonski diagram 100 should they have arisen from photon-mediated electronic transitions. In the presence of a suitable acceptor, the donor fluorophore can transfer excited state energy directly to the acceptor without emitting a photon (illustrated by a horizontal arrow in FIG. 1A). The resulting sensitized fluorescence emission has characteristics similar to the emission spectrum of the acceptor.

Several criteria must be satisfied in order for the resonance energy transfer to occur. In addition to the overlapping emission and absorption spectra of the donor and the acceptor molecules, the two involved fluorophores must be positioned within a range of 1 to 10 nm of each other. As described in equations derived by Förster (and discussed below), the energy transfer efficiency between donor and acceptor molecules decreases as the sixth power of the distance separating the two. Consequently, the ability of the donor fluorophore to transfer its excitation energy to the acceptor by non-radiative interaction decreases sharply with increasing distance between the molecules, limiting the FRET phenomenon to a maximum donor-acceptor separation radius of approximately 10 nm.

The common donor-acceptor dyes pair may include, but not be limited to, Tryptophen-Dansyl, IAEDANS-DDPM, BFP-DsRFP, Dansyl-FITC, Dansyl-Octadecylrhodamine, CFP-GFP, CE-Texas red, Fluorescein-Tetramethylrhodamine, Cy3-Cy5, GFP-YFP, BODIPY FL-BODIPY FL, Rhodamine6G-Malachite Green, FITC-Eosin Thiosemicarbazide, B-Phycoerythrin-Cy5, Cy5-Cy5.5. A typical dye diameter is less than 1 nm.

An additional requirement for the resonance energy transfer is that the fluorescence lifetime of the donor molecule must be of sufficient duration to permit the event to occur. Both the rate $K_T$ and the efficiency E of energy transfer are directly related to the lifetime $\tau_D$ of the donor fluorophore in the presence and the absence of the acceptor. According to Förster's theory, and verified experimentally, the rate of energy transfer is given by the equation: $K_T = (1/\tau_D) \times (R_0/r)^6$, where $R_0$ is the Förster critical distance, $\tau_D$ is the donor lifetime in the absence of the acceptor, and r is the distance separating the donor and the acceptor chromophores. The Förster critical distance $R_0$ is defined as the acceptor-donor separation radius at which the transfer rate equals the rate of donor decay (de-excitation) in the absence of the acceptor. In other words, when the donor and the acceptor separating distance r equals the Förster distance, then the transfer efficiency is 50 percent. FRET efficiency is calculated by the following equation: $E = 1/[1+(r/R_0)^6]$.

Figure 1B:
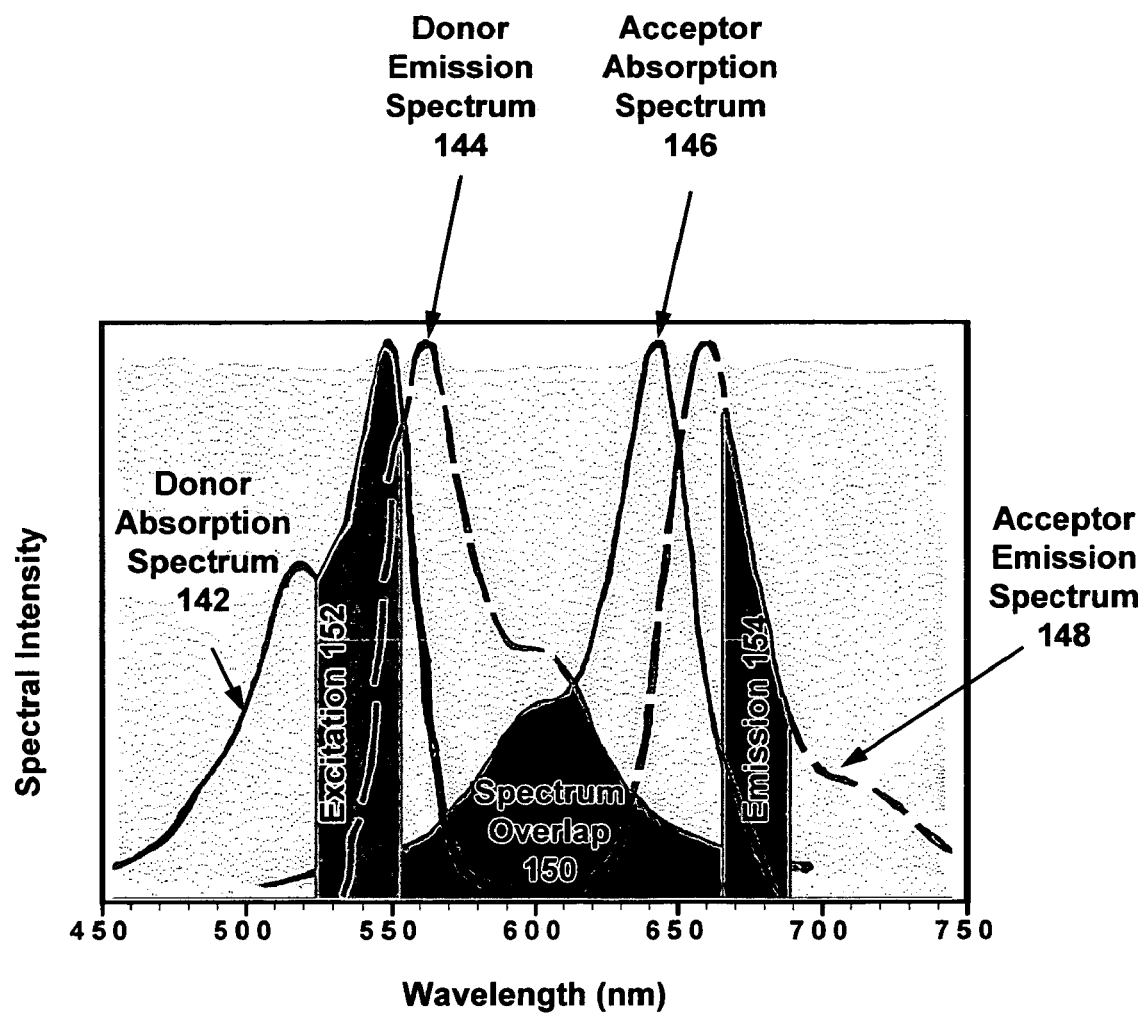
FIG. 1B shows a diagram of the absorption and emission spectrum of an exemplary donor-acceptor dye pair.

Presented in FIG. 1B are the absorption and emission spectra of Cy3 (the donor) 142 and 144, and Cy5 (the acceptor) 146 and 148, when compared to their potential application as a fluorescence resonance energy transfer pair. The region of overlap 150 between the donor emission 144 and the acceptor absorption 146 spectra is represented by a gray area 150 near the base of the curves. Whenever the spectral overlap of the molecules is increased too far, a phenomenon known as spectral bleed-through or crossover occurs in which signals from the excited acceptor (arising from excitation 152 illumination of the donor) and the donor emission are detected in the acceptor emission channel 154. The result is a high background signal that must be extracted from the weak acceptor fluorescence emission.

Figure 1C:
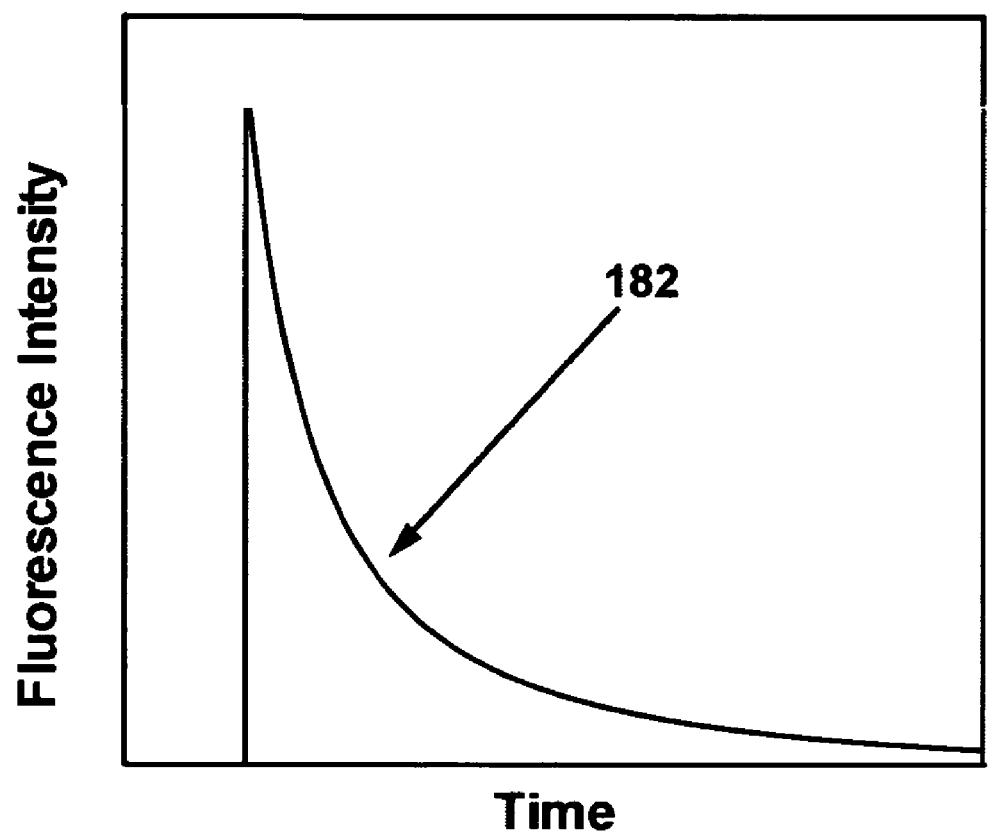
FIG. 1C shows a fluorescence lifetime decay diagram.

Time-domain lifetime measurements employ the pulsed excitation light sources, and the fluorescence lifetime is obtained by directly measuring the emission signal or by photon-counting detection. The specimen is excited by a brief pulse of laser light with duration much shorter than the lifetime of the excited species, and the exponential decay profile 182 is measured as a function of time as shown in FIG. 1C. A typical fluorescence lifetime is about a few nanoseconds.

Embodiments of the present invention are discussed herein with reference to FIGS. 2-6. However, those skilled in the art will readily appreciate that the detailed description given herein with respect to these figures is for explanatory purposes as the invention extends beyond these limited embodiments.

Figure 2:
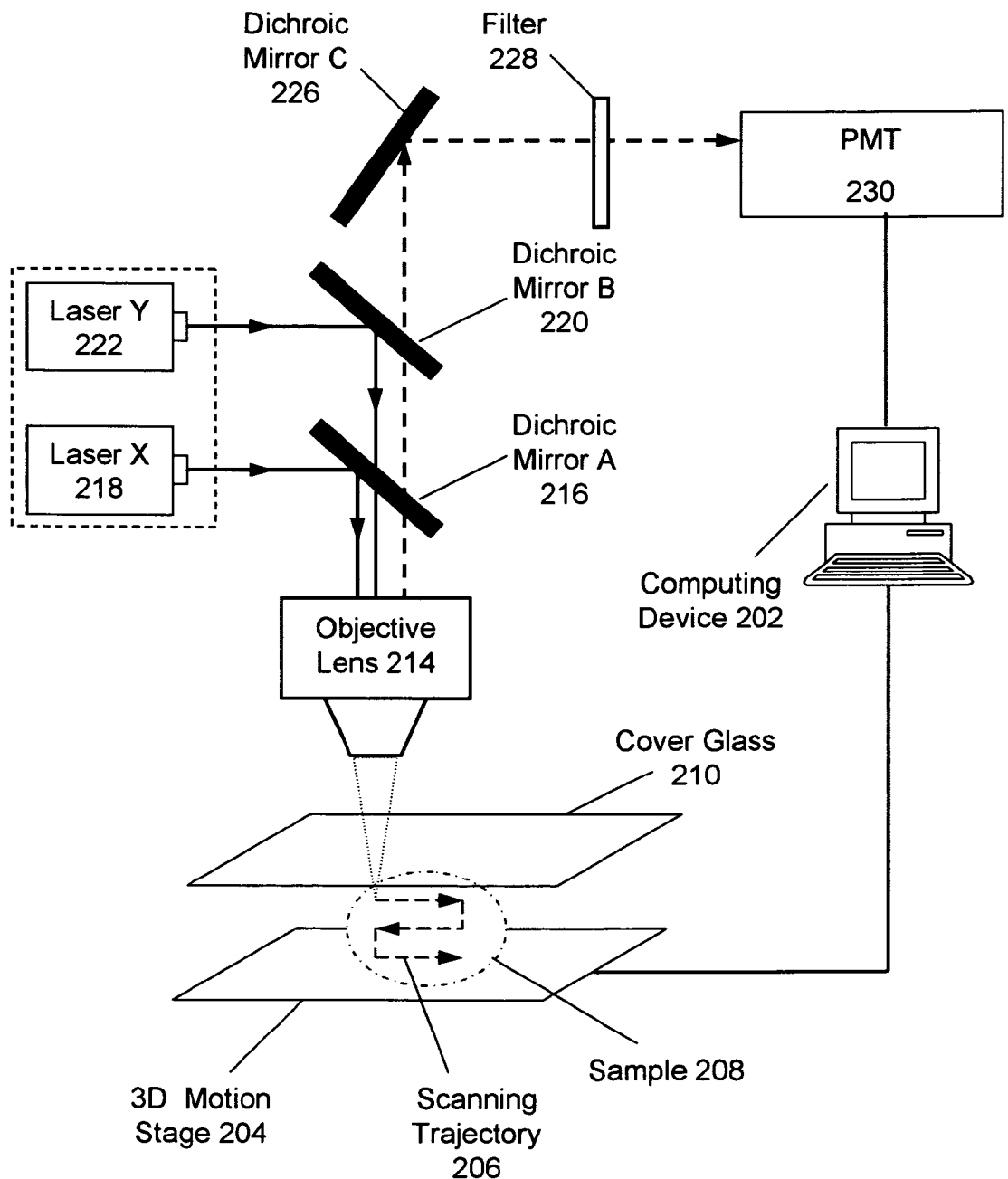
FIG. 2 illustrates the schematic setup diagram of a fluorescence laser scanning microscope in accordance with an embodiment of the present invention.

Referring now to the drawings, in which like numerals refer to like parts throughout several views. FIG. 2 illustrates the schematic setup diagram of a fluorescence laser scanning microscope 200 in accordance with an embodiment of the present invention. In this embodiment, the microscope 200 includes a computing device or a computer 202 used for controlling a three-dimensional (3D) motion stage 204, in which a sample or object 208 (e.g., a live cell) is placed for laser scanning. The computer 202 moves the 3D motion stage 204 so that the sample 208 will be scanned in a trajectory 206 to enable the computer 202 to create a 3D image of the sample 208 in its memory or storage. The sample 208 used in this embodiment is a live cell labeled with a plurality of nanoparticles, which were co-doped with a controlled amount of donor and acceptor dyes. In one embodiment, silica nanoparticles having a diameter of 2.5 nm are used. In another embodiment, the donor-acceptor dyes pair is selected such that FRET is guaranteed to occur between them when a laser pulse shines the nanoparticles with a frequency close to the peak absorption spectrum of the acceptor. Further included in the microscope 200 is a cover glass 210, an objective lens 214, a set of three dichroic mirrors 216, 220 and 226, a filter 228, two laser sources 218 and 222, and a photo-multiple tube (PMT) 230. The sample 208 is placed underneath the transparent cover glass 210, so that the sample 208 can be observed. The objective lens 214 is located directly above the laser scanning point. Each location of interest along the scanning trajectory 206 is placed directly in the center of the objective lens 214 one at a time. The distance between the location of interest and the aperture of the objective lens 214 determines the numerical aperture. In order to observe the smallest possible object, the largest feasible numerical aperture is chosen such that the resulting focal spot corresponds to the diffraction limit in this embodiment.

In this embodiment, the present invention requires two laser pulses at each location of interest in the scanning trajectory 206 of the sample 208. These two laser pulses have different center wavelengths and durations. The first laser pulse is configured to ensure a pre-determined amount of the donors get excited and the first FRET process between some of the excited donors and the acceptors will occur, while the second laser pulse is configured to accelerate the energy depletion of the excited acceptors due to the first FRET process.

In one embodiment, the first laser pulse has a center wavelength near the peak of the absorption spectrum of the acceptor (e.g., 550 nm 152 in FIG. 1B) and a very short duration (e.g., 100 fs). The duration of the first laser pulse should be significantly shorter than the FRET time-decay lifetime of the donor (e.g., 30 ps). The second laser pulse has a center wavelength near the extreme value of the emission spectrum of the acceptor (e.g., 680 nm 154 in FIG. 1B) and a duration (e.g., 1 ps) that is significantly shorter than the FRET time-decay lifetime of the donor, but it still can be effectively blocked out by a filter because of its narrow spectrum such that the fluorescence emission can be detected without interference.

The first laser pulse is shot from the laser source X 218 towards the dichroic mirror A 216 onto sample 208 through the objective lens 214. It is noted that the focal spot of the first laser pulse is controlled to be as small as possible in accordance with the diffraction limit of the laser light. The second laser pulse, which has a reduced beam size for generating a focal spot size much larger than that of the first laser pulse, is shot from the laser source Y 222 towards dichroic mirror B 220 onto the sample 208. Dichroic mirror A 216 is configured to facilitate the high reflection of the first laser pulse and to facilitate the high transmission of the second laser pulse and the fluorescence emission from the acceptors. Dichroic mirror B 220 is configured to facilitate the high reflection of the second laser pulse and to facilitate the high transmission of the fluorescence emission from the acceptors. It is noted that the first laser source X 218 and the second laser source Y 222 may be housed in one compartment in accordance with another embodiment.

In this embodiment, the fluorescence emission from the acceptors travels through the cover glass 210, the objective lens 214, and the dichroic mirrors A 216 and B 220 towards the dichroic mirror C 226 that is set up to facilitate the high reflection of the fluorescence emission and the high transmission of other lights. The fluorescence emission passes through filter 228 that will blocked out all other lights except the fluorescence emission from the acceptors, which is recorded by computing device 202 via PMT 228.

Figure 3A:
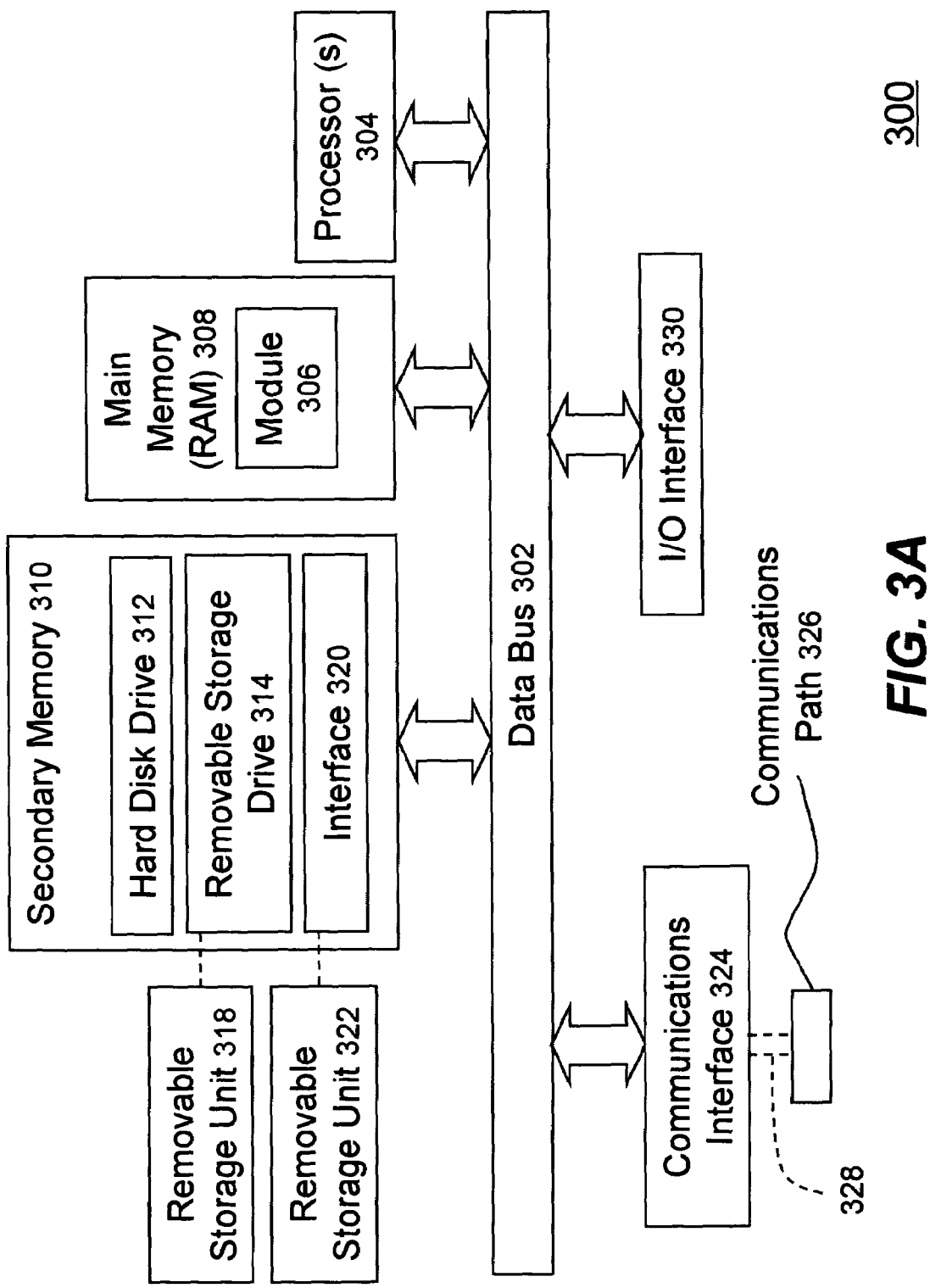
FIG. 3A shows a block diagram of a computing device, in which the present invention is executable by a processor according to one embodiment.

The present invention requires a computer system or other processing system to control the laser scanning of a 3D sample placed in a 3D motion stage (e.g., 204 of FIG. 2). In fact, in one embodiment, the invention is directed towards one or more computer devices capable of carrying out the functionality described herein. An example of a computer device 300 is shown in FIG. 3A (e.g., the computing device 202 of FIG. 2). In this document, the computer device, computer, and the computer system are used interchangeably hereinafter. The computer system 300 includes a processor 304. The processor 304 is connected to a computer device internal communication bus 302. Various software embodiments are described in terms of this exemplary computer system. After reading this description, it will become apparent to a person skilled in the relevant art(s) on how to implement the invention using other computer systems and/or computer architectures.

Computer system 300 also includes a main memory 308, preferably random access memory (RAM), and may also include a secondary memory 310. The secondary memory 310 may include, for example, one or more hard disk drives 312 and/or one or more removable storage drives 314, representing a floppy disk drive, a magnetic tape drive, an optical disk drive, etc. The removable storage drive 314 reads from and/or writes to a removable storage unit 318 in a well-known manner. Removable storage unit 318, represents a floppy disk, magnetic tape, optical disk, etc., which is read by and written to a removable storage drive 314. As will be appreciated, the removable storage unit 318 includes a computer usable storage medium having stored therein computer software and/or data.

In alternative embodiments, secondary memory 310 may include other similar means for allowing computer programs or other instructions to be loaded into computer system 300. Such means may include, for example, a removable storage unit 322 and an interface 320. Examples of such may include a program cartridge and cartridge interface (such as that found in video game devices), a removable memory chip (such as an EPROM, or PROM) and associated socket, and other removable storage units 322 and interfaces 320 which allow software and data to be transferred from the removable storage unit 322 to computer system 300. In general, computer system 300 is controlled and coordinated by operating system (OS) software, which performs tasks such as process scheduling, memory management, networking and I/O services. Exemplary OS includes Linux®, Microsoft Windows®, etc.

There may also be a communications interface 324 connecting to the bus 302. Communications interface 324 allows software and data to be transferred between computer system 300 and external devices. Examples of communications interface 324 may include a modem, a network interface (such as an Ethernet card), a communications port, a PCMCIA slot and card, etc. Software and data transferred via communications interface 324 are in the form of signals 328 which may be electronic, electromagnetic, optical, or other signals capable of being received by communications interface 324. These signals 328 are provided to communications interface 324 via a communications path (i.e., channel) 326. This channel 326 carries signals (or data flows) 328 and may be implemented using wire or cable, fiber optics, a phone line, a cellular phone link, an RF link and other communications channels.

The channel 326 facilitates a data flow 328 between a data network and the computer 300 and typically executes a special set of rules (i.e., a protocol) to send data back and forth. One of the common protocols is TCP/IP (Transmission Control Protocol/Internet Protocol) which is commonly used in the Internet. In general, the communication interface 324 manages the assembling of a data file into smaller packets that are transmitted over the data network or reassembles received packets into the original data file. In addition, the communication interface 324 handles the address part of each packet so that it gets to the right destination or intercepts packets destined for the computer 300.

In this document, the terms "computer program medium" and "computer usable medium" are used to generally refer to media such as a flash memory 312, and signals 328. These computer program products are means for providing software to computer system 300. The invention is directed to such computer program products. The computer system 300 may also include an I/O interface 330, which allows the computer system 300 to access monitor, speaker, microphone, video camera, keyboard, mouse, printer, scanner, plotter, speaker, and the like.

Computer programs (also called computer control logic) are stored as application modules 306 in main memory 308 and/or flash memory 312. Computer programs may also be received via communications interface 324. Such computer programs, when executed, enable the computer system 300 to perform the features of the present invention as discussed herein. In particular, the computer programs, when executed, enable the processor 304 to perform the features of the present invention. Accordingly, such computer programs represent controllers of the computer system 300.

In an embodiment where the invention is implemented using software, the software may be stored in a computer program product and loaded into computer system 300 using flash memory 312, or communications interface 324. The application module 306, when executed by the processor 304, causes the processor 304 to perform the functions of the invention as described herein.

Figure 3B:
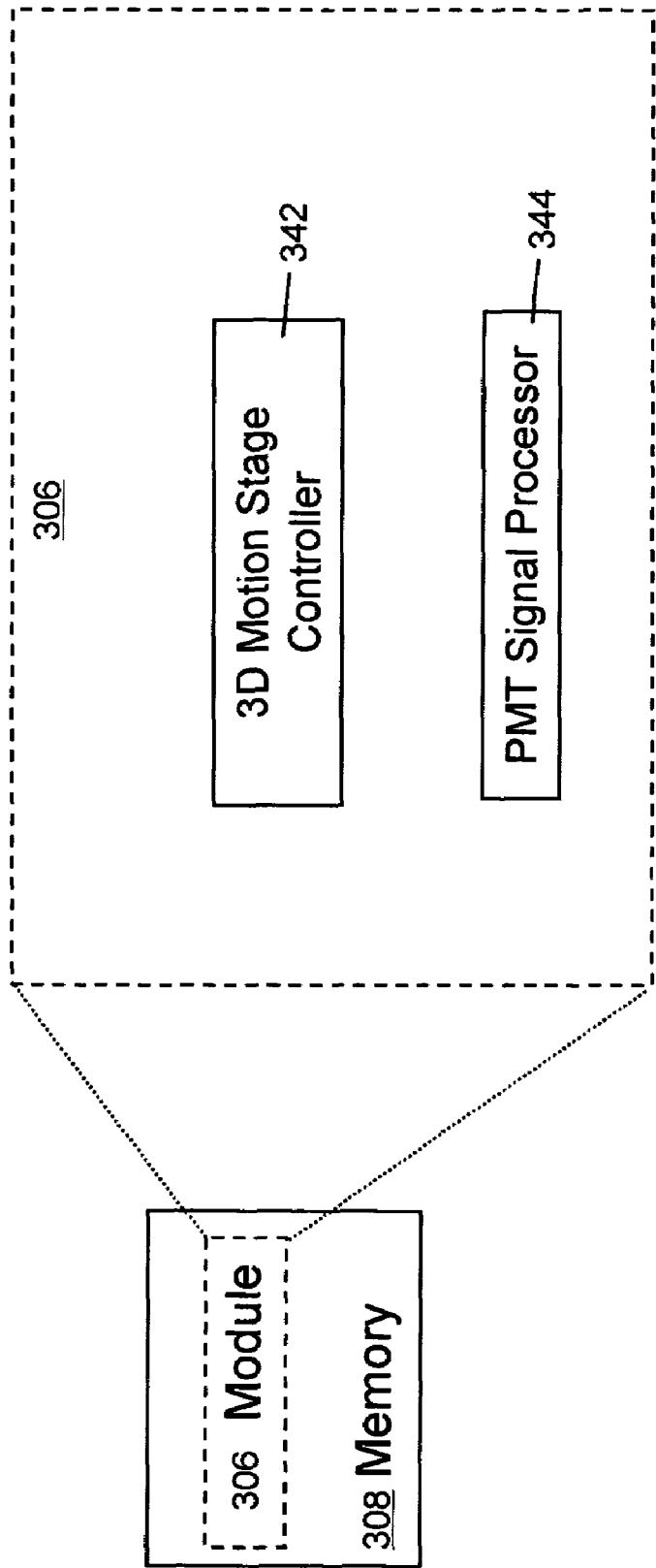
FIG. 3B shows software modules in the memory of a computing device in accordance with one embodiment of the present invention.

Referring now to FIG. 3B, the functional block diagram of application modules 306 residing in the memory 308 of a computing device (e.g., computer system 300 of FIG. 3A) is shown. In accordance with one embodiment of the present invention, the application modules include a 3D motion stage controller 342 and a PMT signal processor 344. These two components may be combined into one module in other embodiments. The 3D motion stage controller 342 controls the 3D motion stage such that the sample placed in the stage is laser scanned in a pre-determined scanning trajectory. At each scanned location along the trajectory, PMT detects and records the fluorescence emission from the sample to construct a 3D image of the sample in the memory or storage of the computer 300. These functions can be performed by a general purpose computer or a specially built computer or any other computing device that can perform these two functions according to the embodiments of the present invention.

Figure 4A:
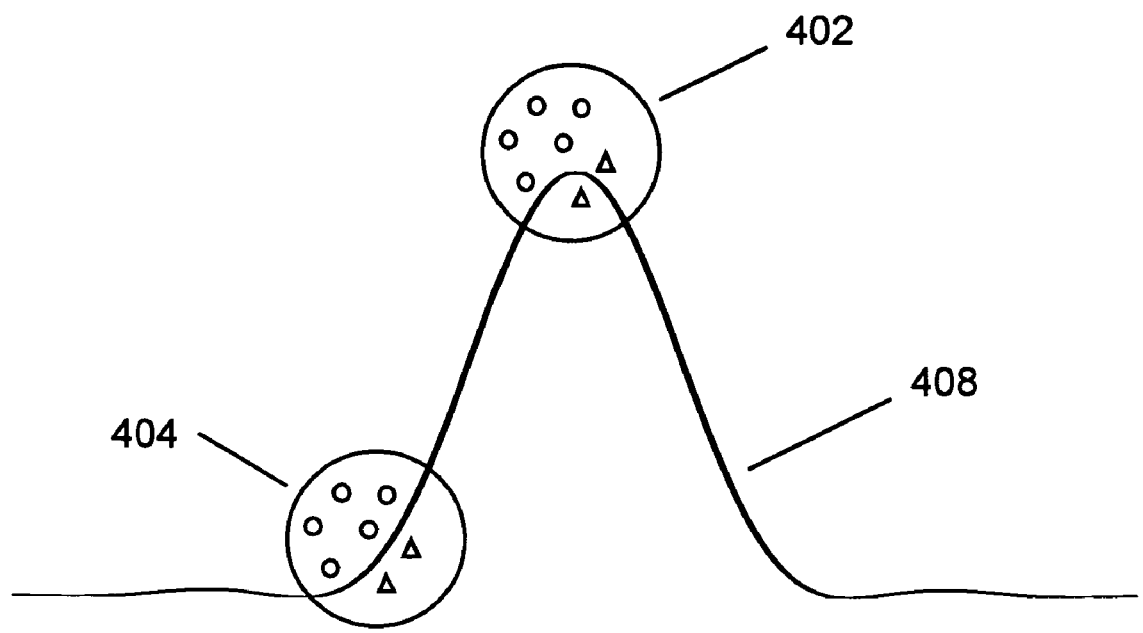
FIGS. 4A-4F schematically illustrate the concept of FRET-IED microscopy in accordance with one embodiment of the present invention.
Figure 4B:
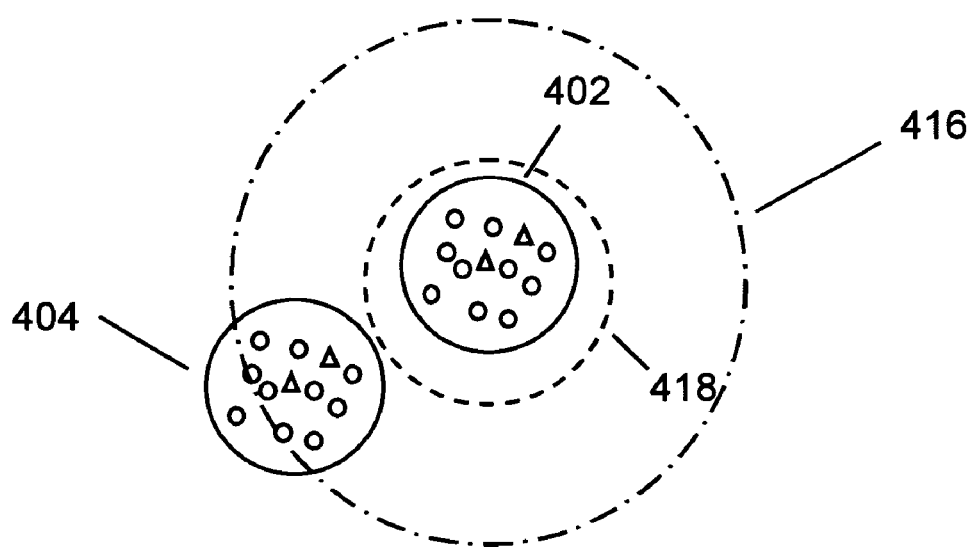

FIGS. 4A-4F schematically illustrate the concept of the FRET-IED microscopy 200 in accordance with one embodiment of the present invention. To simplify the explanation in this embodiment, only two silica nanoparticles A 402 and B 404 are used. In reality, there are generally a large number of nanoparticles under a laser scanning operation of the FRET-IED microscope. These two nanoparticles are located very close to each other within an area smaller than the diffraction-limited focal spot of the exciting laser (e.g., the first laser pulse of FIG. 2) as shown in an elevation view in FIG. 4A. This means that the two nanoparticles are too close to be able to be distinguished with any conventional optical microscope due to the diffraction limit of a laser light. The curve 408 represents the laser intensity distribution in the focal spot 416 of the laser pulse. In this example, nanoparticle A 402 is located in a small circular area 418 at the center of the focal spot, while nanoparticle B 404 is at the outer part of the focal spot 416 as shown in FIG. 4B. In the embodiment, the area of the focal spot 416 is limited by the diffraction limit; therefore the smaller circular area 418 within the focal spot is smaller than the diffraction limit. In this embodiment, each of the nanoparticles is co-doped with five donors (hollow circle) and two acceptors (hollow triangles) as shown in FIG. 4A. A Cy3-Cy5 donor-acceptor dyes pair is used in the example. It is noted that the figures are not in scale for the examples shown in FIGS. 4A-4F.

Figure 4C:
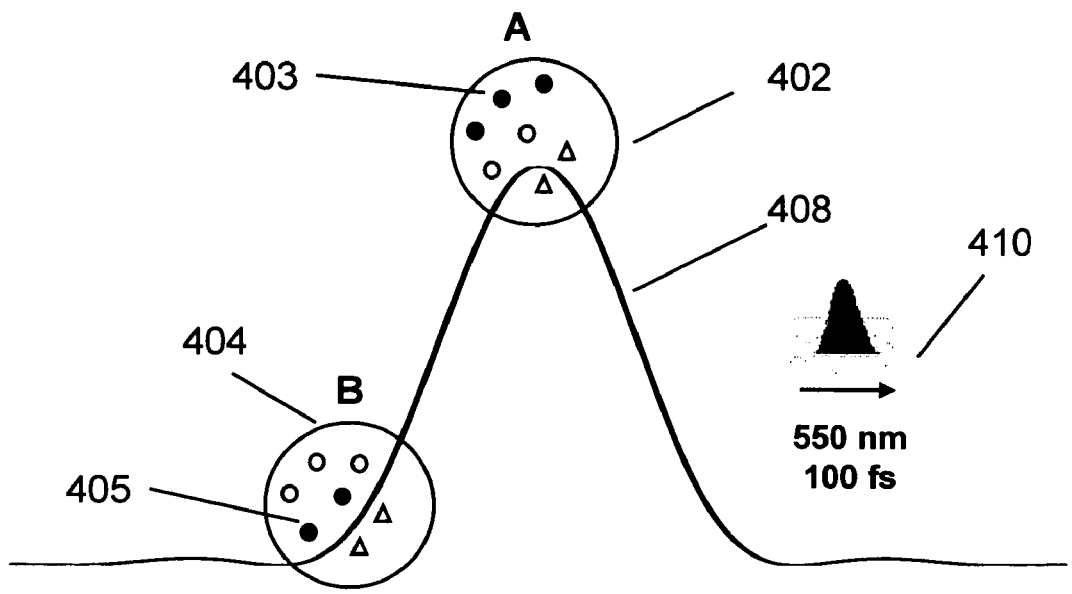
Figure 4D:
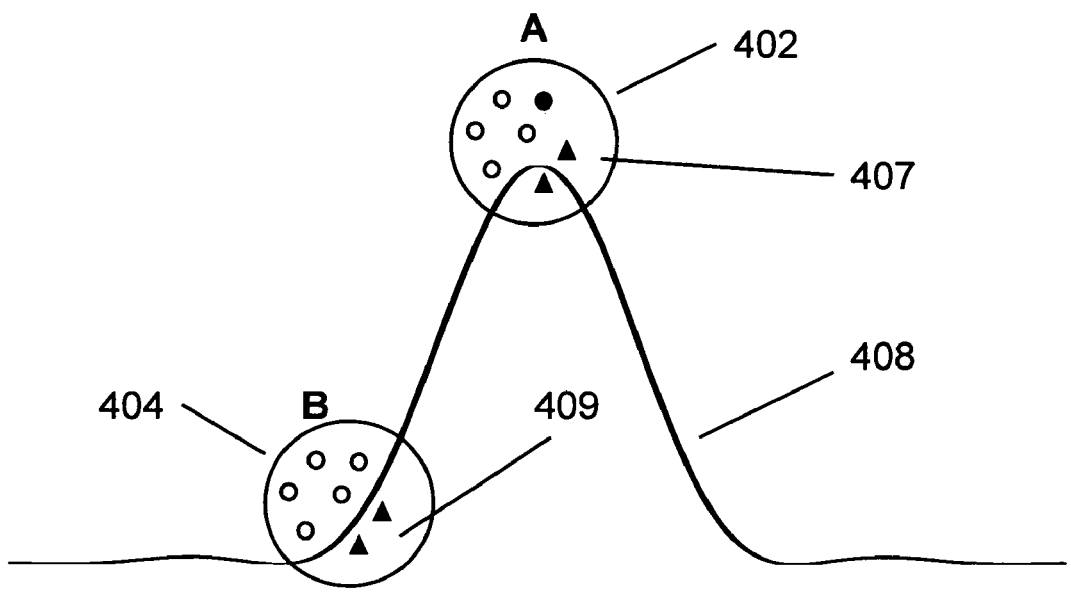

Next in this embodiment, the sample with two nanoparticles is excited by a first laser pulse 410, whose center wavelength is 550 nm and 100 fs duration. This first laser pulse excites donors in nanoparticles A 402 and B 404 as shown in FIG. 4C. It is noted that the peak of the absorption spectrum of the acceptor, Cy5, is near 550 nm. With a careful control of the laser intensity, three donors represented by solid circle 403 have been excited in nanoparticle A 402, while two donors 405 have been excited in nanoparticle B 404. The reason is that nanoparticle A 402 is located at a small circular area 418 in the center of the focal spot of the first laser pulse 416. The laser intensity is higher in the center than that in the edge of the focal spot as indicated by the Airy pattern 408. Immediately after applying the first laser pulse, a first FRET process occurs between donors and acceptors. The lifetime duration for the first FRET process can be evaluated using the following equation: $\tau = \tau_0 \times (1-E)$, where $\tau_0$ is the donor's lifetime in absence of an acceptor and E is the FRET efficiency. A typical fluorescence lifetime of a Cy3 dye donor in absence of an acceptor is about 2 ns. Using the Förster critical distance of 5 nm for the Cy3-Cy5 pair and a 2.5 nm diameter nanoparticle, the FRET efficiency is about $98.44\% = 1-(2.5/5)^6$. The lifetime duration of the first FRET process can be calculated as follows: $2000 \times (1-0.9844)$, which is about 30 ps. FIG. 4D shows the state of nanoparticles A 402 and B 404 at 100 ps after applying the first laser pulse. All but one donor in nanoparticle A 402 have transferred their energy to the acceptors 407 represented by solid triangles, while all donors in nanoparticle B 404 have transferred their energy to the acceptors 409 represented by solid triangles. The reason that one donor in nanoparticle A 402 has not transferred its energy to the acceptor is because the first FRET process is saturated in the small circular central area 418 by design in accordance with one embodiment of the present invention. In other embodiments, there may be different ratios of donors and acceptors used for preparing co-doped nanoparticles. Hence, the number of the donors remains in the excited state after the first FRET process may be more than one as depicted in FIG. 4D.

Figure 4E:
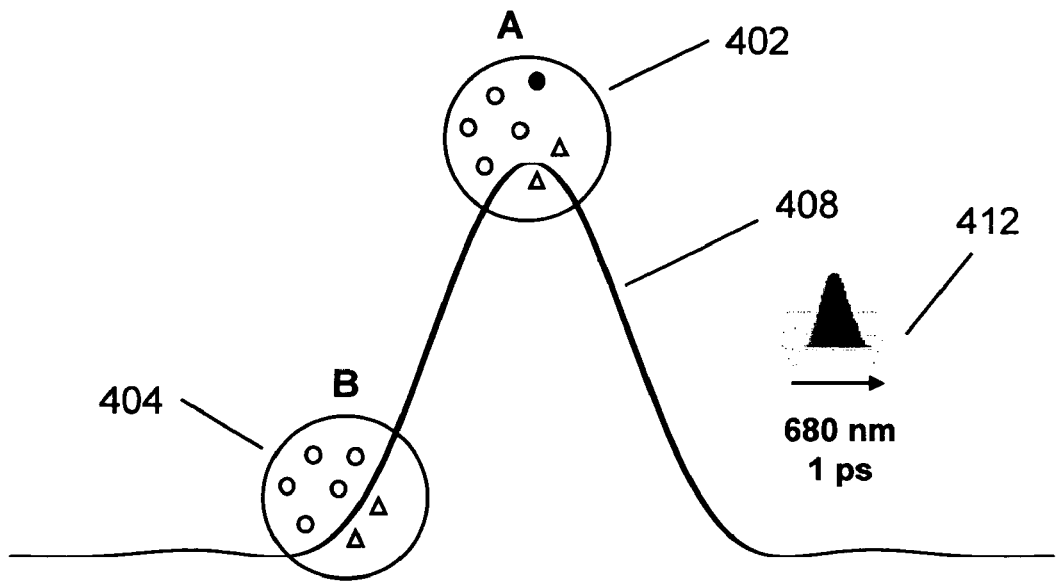

FIG. 4E shows the next step according to this embodiment. A second laser pulse is applied to the same focal spot of the first laser pulse. The second laser pulse has a wavelength near the extreme value of the emission spectrum of the acceptor and a very short duration as compared to the first FRET lifetime duration. In this example, the second laser pulse has a 680 nm center wavelength and 1 ps duration. As a result of applying the second laser pulse, all of the excited acceptors due to the first FRET process as shown in FIG. 3D have depleted their energy very rapidly, much faster than the natural fluorescence emission process. The intensity of the second laser pulse should be uniform throughout the focal spot of the first laser pulse to ensure that all excited acceptors 407 and 409 in both nanoparticles A 402 and B 404 are depleted.

Figure 4F:
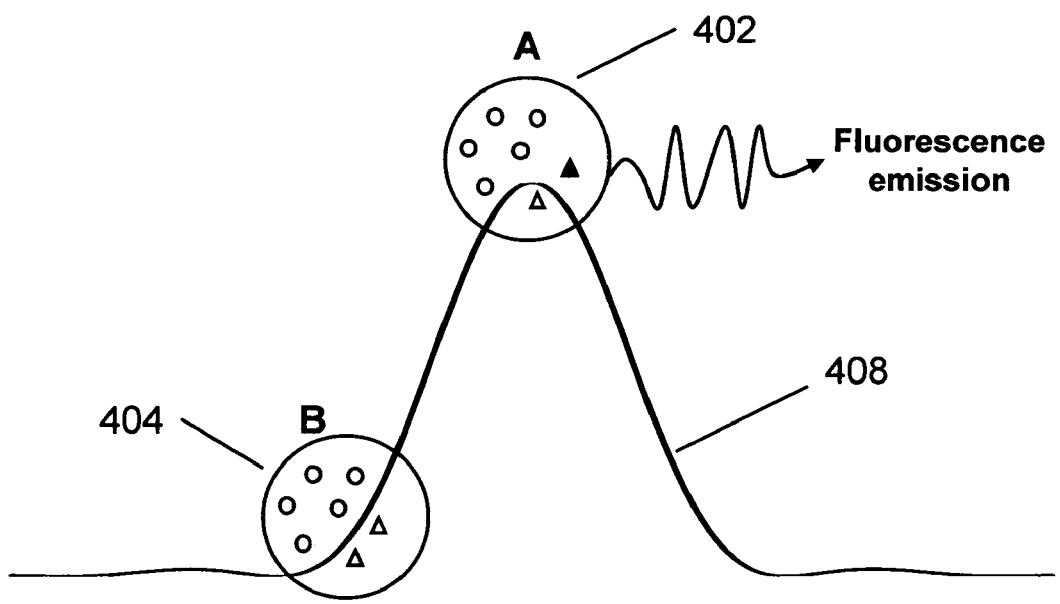

After applying the second laser pulse, a second FRET process occurs between the remaining already excited donors and the newly depleted acceptors in nanoparticle A 402, as shown in FIG. 4F. The computer (202 of FIG. 2) detects and collects the fluorescence emitted from the acceptor via PMT (230 of FIG. 2) to construct a 3D image of the sample with finer details because the fluorescence emission is only from the central small circular area 418 of the focal spot. Because the focal spot 416 of the first laser pulse is based upon the diffraction limit, the fluorescence emission from an area smaller than the focal spot is below the diffraction limit. In this embodiment, nanoparticle A 402 is located inside the central small circular area 418 that fluorescence emission is detected. Nanoparticle B 404 is located in an outer portion of the focal spot 416, in which there is no more fluorescence emission any more due to the excitations of the two laser pulses. In other embodiments, there may be more than one nanoparticle located in the central small circular area 418 of the focal spot 416. Additionally, in this embodiment, the second laser pulse has 1 ps duration with a bandwidth about 1 nm, which is much narrower than that of the acceptor's fluorescence emission spectrum. A filter (228 of FIG. 2) can be used to effectively block out the reflections resulted from the first and second laser pulses.

It is noted that a 2.5 nm nanoparticle has a volume that is about 15 times of a dye of 1 nm in diameter. Also, if the dye is too large, there can not be a FRET process between the donor and acceptor dyes pair.

Figure 5A:
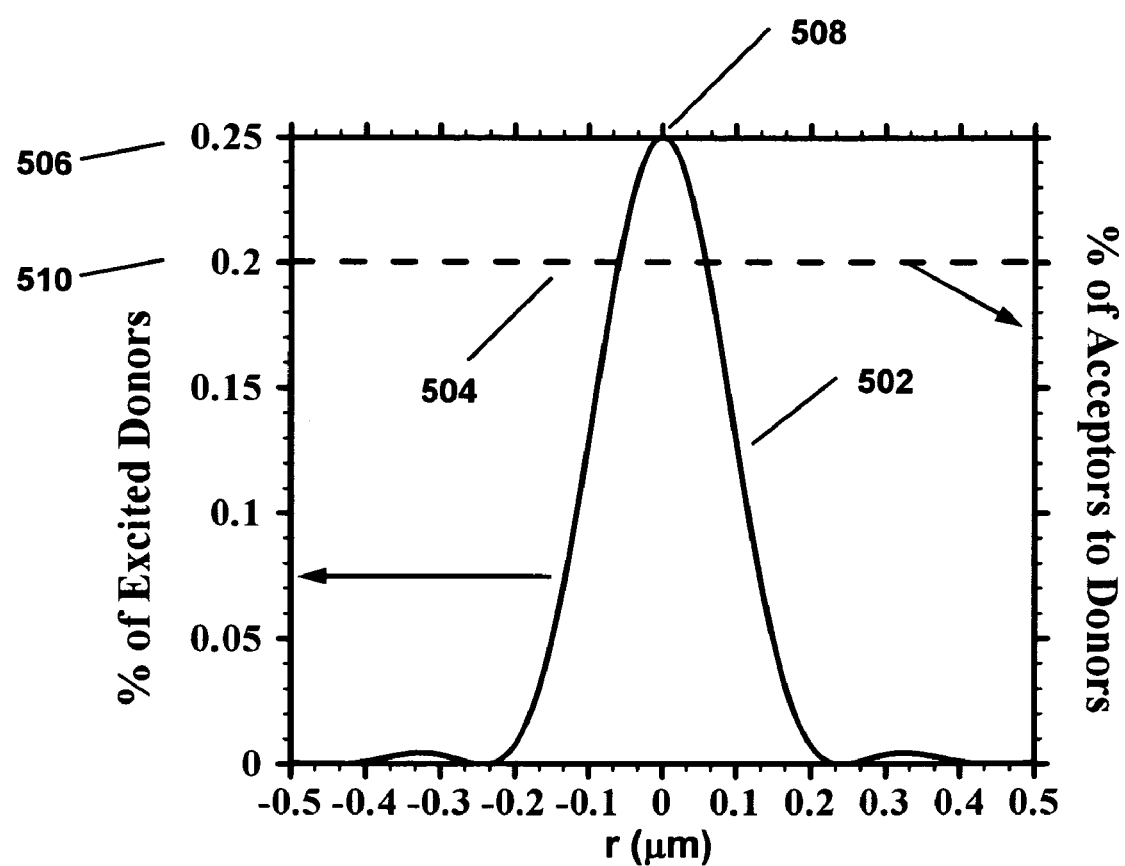
FIGS. 5A-C show an exemplary demonstration as to how a FRET-IED microscopy exceeds the diffraction-limit resolution in accordance with one embodiment of the present invention.
Figure 5B:
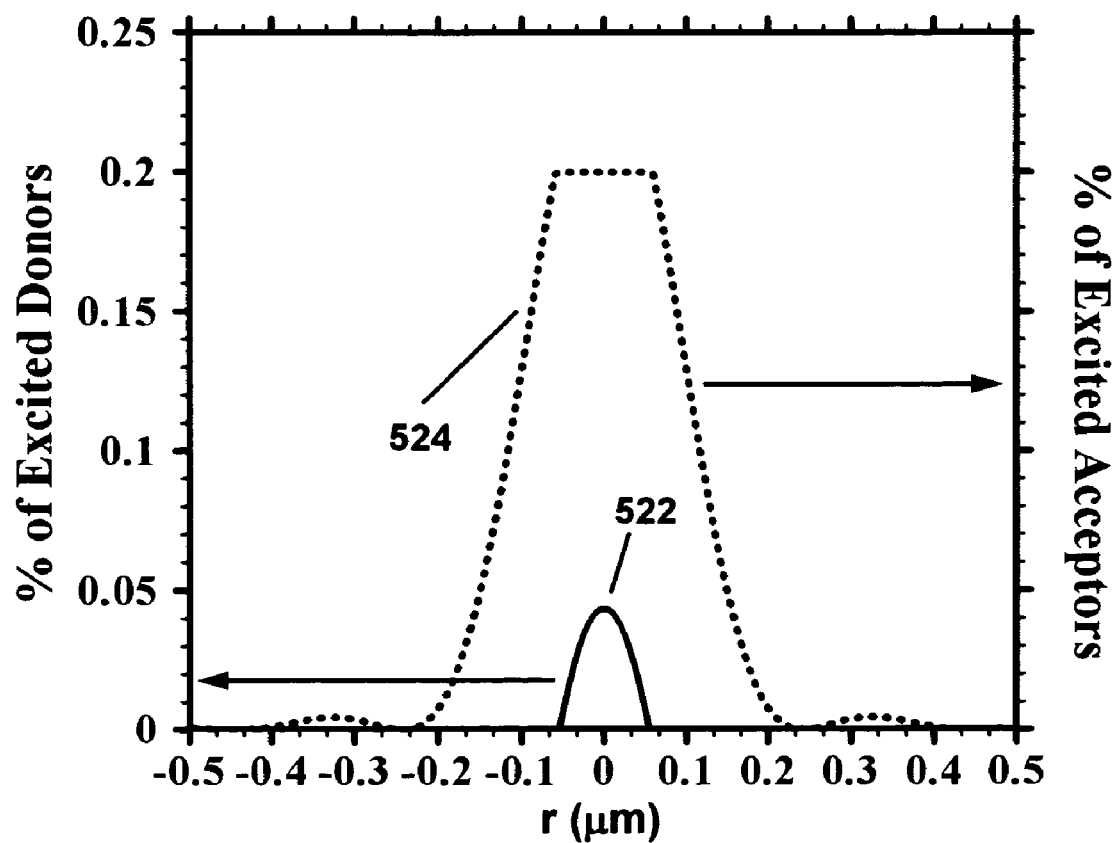
Figure 5C:
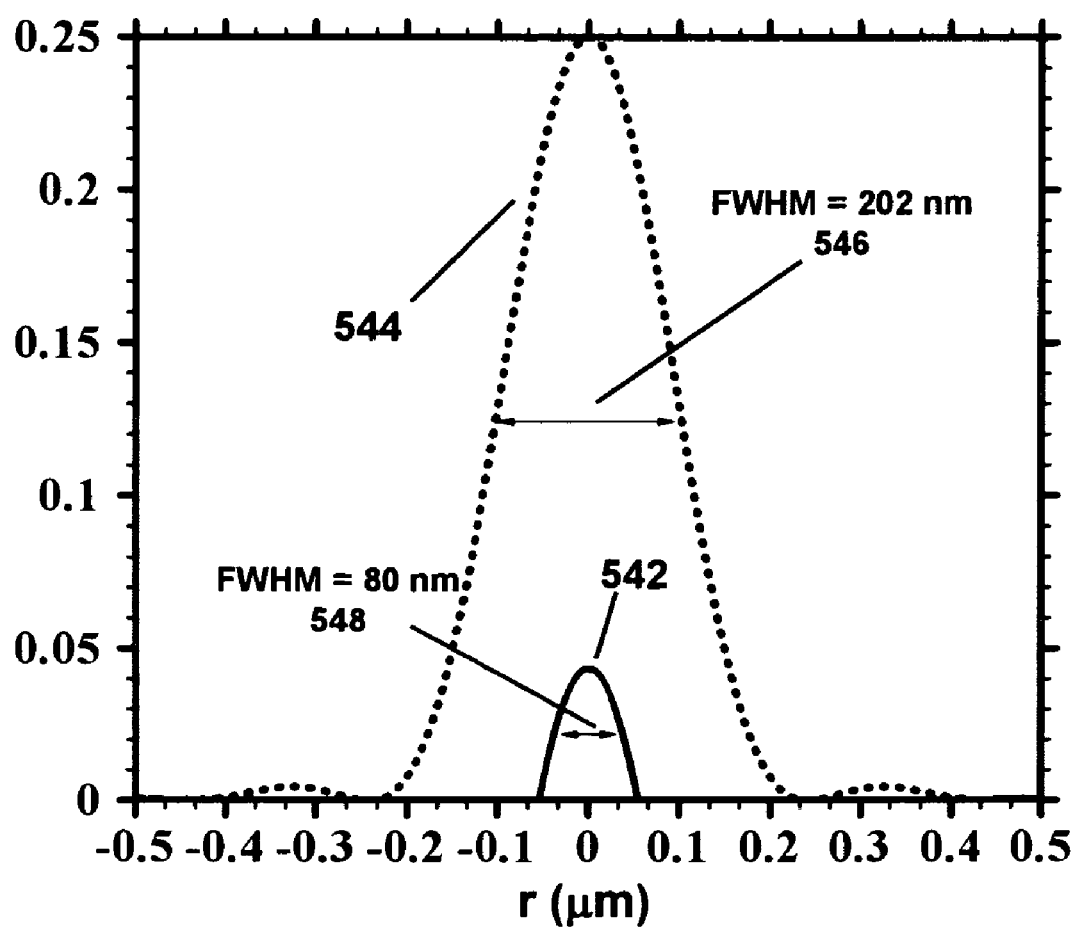

FIGS. 5A-5C demonstrate how a FRET-IED microscopy exceeds the diffraction-limit resolution with an exemplary calculation in accordance with one embodiment of the present invention. In this embodiment, the donor acceptor dyes pair is Cy3 and Cy5, respectively. The ratio between donors and acceptors co-doped on a nanoparticle is assumed to be 5:1. The first laser pulse, which has a pulse duration of 100 fs and a center wavelength of 550 nm in this exemplary calculation, is focused by a high numerical aperture (NA=1.4) oil-immersion objective lens to form a diffraction-limited focal spot (416 of FIG. 4B). The excitation energy of the fist laser pulse is carefully adjusted to obtain a peak at 25% excitation efficiency 506 of the donor dyes at the center 508 of the focal spot. At such a sub-saturation excitation rate, the excitation efficiency can be considered to be proportional to the laser intensity. Thus, immediately after the first laser pulse, the quantity of the excited donors in a nanoparticle is proportional to a function (e.g., airy shape) of the position of the nanoparticle in the focal spot, as shown in the solid curve 502 in FIG. 5A. The dashed line 504 in FIG. 5A shows the quantity of the acceptors at the ground state, which is constant throughout the focal spot at 20% 510 or ⅕. At 100 ps after applying the first laser pulse, all of the excited donors will have completely transferred their energy to the acceptors, resulting in a decreased quantity of excited donors 522 but an increased quantity of the excited acceptors 524 due to a first FRED process between donors and acceptors, as shown in FIG. 5B. Next, a second laser pulse is applied to accelerate the energy depletion of the excited acceptors due to the first FRED process. The second laser pulse used in this exemplary calculation has a center wavelength of 680 nm with 1 ps duration. To ensure the uniform depletion efficiency for all of the nanoparticles inside the focal spot of the first laser pulse, the second laser pulse should be loosely focused by reducing its laser beam size at the back aperture of the objective lens. For example, if one assumes the beam diameter of the second laser pulse is reduced to 1/10 of the diameter of the back aperture, the actual numerical aperture of the second laser pulse decreases from 1.4 to approximately 0.34 so that the focal spot size of the second laser pulse is four times larger than that of the first laser pulse in the lateral direction and sixteen times larger in the axial direction. Therefore, the laser intensity of the second laser pulse is considered evenly distributed in the excitation focal spot of the first laser pulse. Assuming a typical stimulated emission cross section of $10^{-16}$ cm$^2$ for Cy5, one can easily obtain the photon flux of the second laser pulse required for reducing the quantity of the excited acceptors to 1% of its original value, which is approximately equal to 13 mJ/cm$^2$. This relatively low depletion energy is one of the benefits of the FRET-IED microscopy, reducing both the photobleaching and the phototoxicity. After applying the second laser pulse, the remaining excited donors can transfer their energy to the acceptors again in a second FRET process. After the completion of this second FRET process, the quantities of the acceptors 542 at the excited state are shown in FIG. 5C. It clearly shows that only the fluorescent nanoparticles located at the central area (e.g., the small area 418 of FIG. 4B) of the focal spot (e.g., 416 of FIG. 4B) of the first laser pulse are now able to emit fluorescence, leading to a significantly reduced excitation volume when compared to the "classic" diffraction-limited focal spot 544. As indicated in FIG. 5C, the half-width-at-full-maximum (HWFM) of the focal spot (lateral direction) produced by the first laser pulse is 202 nm 546; whereas the HWFM of the central small circular area in accordance with this embodiment of the present invention is only 80 nm 548, resulting in a 2.5-fold enhanced of lateral resolution. In other embodiments, different donor acceptor pairs along with different laser pulses yield other enhancement exceeding the diffraction-limit resolution.

Figure 6:
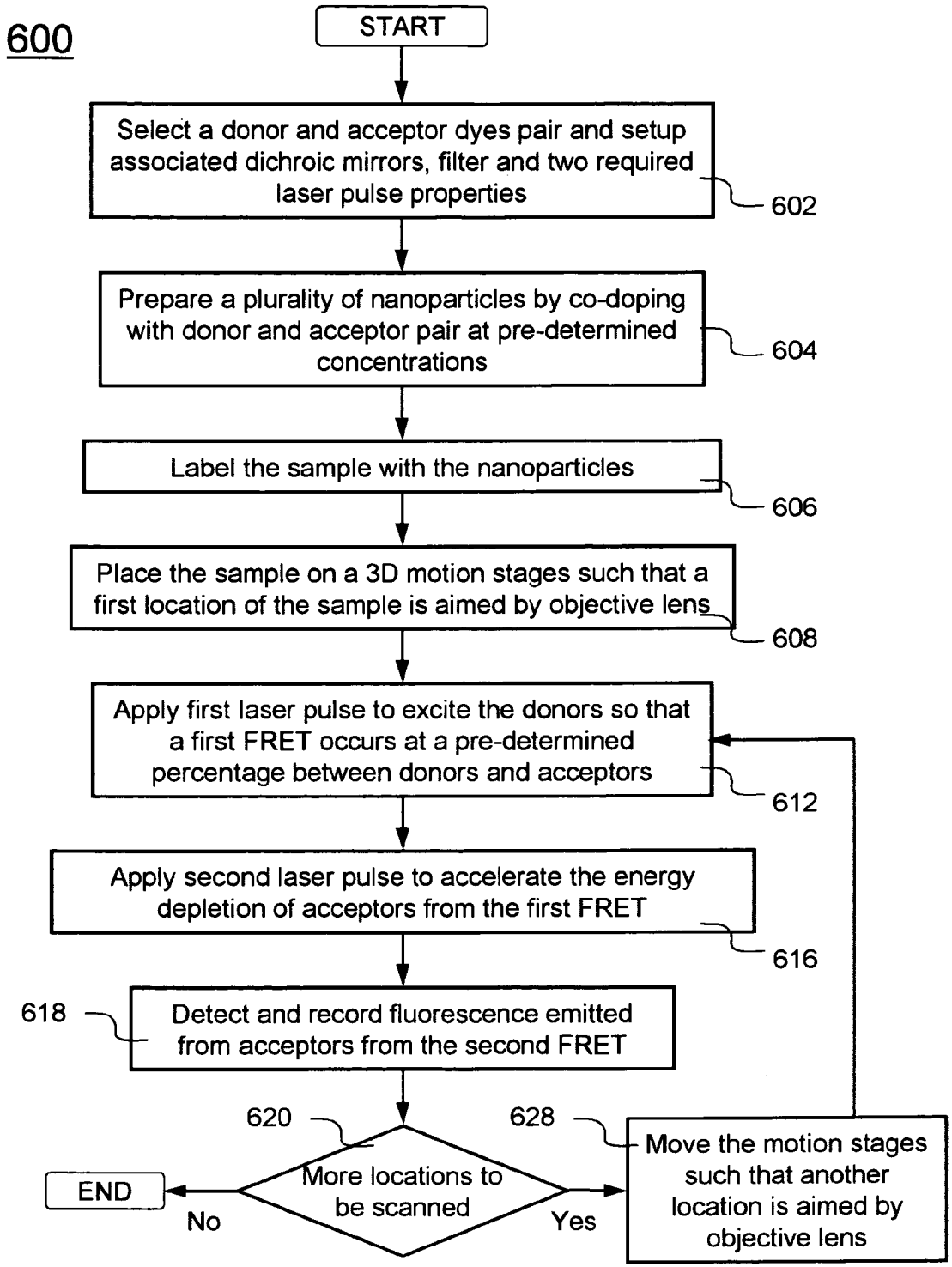
FIG. 6 shows a flow diagram or process of exceeding diffraction-limit resolution in a FRET-IED microscopy in accordance with one embodiment of the present invention.

FIG. 6 shows a flow diagram or process 600 of exceeding diffraction-limit resolution in a FRET-IED microscopy in accordance with one embodiment of the present invention. The process 600, which is preferably understood in conjunction with previous figures especially with FIGS. 2, 4A-4F and 5A-5C. In this embodiment, the process 600 starts with selecting a donor acceptor dyes pair that is suitable for the sample or object of interest at 602. With the selection of the donor-acceptor pair (e.g., Cy3-Cy5), the properties (e.g., wavelength and duration) of the two laser pulses to be used in the laser scanning can be determined. Accordingly, a set of three dichroic mirrors (e.g., dichroic mirrors 216, 220, 226 of FIG. 2) and a filter (e.g., 228 of FIG. 2) can also be selected and setup properly in the FRET-IED microscopy. Then at 604, the process 600 prepares a plurality of suitable transparent nanoparticles by co-doping with a pre-determined controlled concentration of donors and acceptors. The suitable nanoparticles may include, but not be limited to, silica, latex, and the like. In this embodiment, the nanoparticle needs to have a diameter smaller than one-half of the Förster critical distance of the donor-acceptor dyes pair. Also in this embodiment, the ratio of the pre-determined controlled concentration of donors and acceptors is pre-determined to 5:1. The number of donors needs to be more than that of the acceptors. Process 600 uses the plurality of the nanoparticles to label the sample of interest at 606. Next at 608, the labeled sample is then placed on a 3D motion stage (e.g., 204 of FIG. 2) such that a number of locations of interest in the sample can be laser scanned in a trajectory (e.g., 206 of FIG. 2) to create a 3D image in a computing device (e.g., 202 in FIG. 2).

At 612, process 600 applies a first laser pulse to the sample via a first dichroic mirror and objective lens. The numerical aperture (NA) of the objective lens needs to be set to the highest (e.g., NA=1.4), such that the focal spot of the first laser pulse is the smallest area that the diffraction limit permits. The first dichroic mirror (e.g., dichroic mirror A 216 of FIG. 2) is configured to facilitate the high reflection of the first laser pulse and high transmission of other lights. The first laser pulse has a first wavelength and a first duration. The first wavelength should be near the peak of the absorption spectrum of the acceptor. The first duration (e.g., 100 fs) should be significantly shorter than the first FRET lifetime of the donor (e.g., 30 ps). The intensity of the first laser pulse is controlled to ensure that the first FRET process only occurs with saturation in the central small circular area of the focal spot of the first laser pulse. In this embodiment, the first laser intensity is set to 25% for the 5:1 ratio donor/acceptor concentration, so that the saturation of the first FRET process occurs in the area where the first laser intensity is greater than 20%.

After a period (e.g., 100 ps) that is longer than the first FRET lifetime of the donor, process 600 applies a second laser pulse at the same location (i.e., the focal spot of the first laser pulse) of the sample at 616. The numerical aperture of the objective lens should be set to a lower value (e.g., NA=0.34) to ensure the intensity of the second laser pulse to be uniform throughout the focal spot of the first laser pulse. The second laser pulse is applied to the sample via the second dichroic mirror (e.g., dichroic mirror B 220 of FIG. 2) and through the objective lens. The second laser pulse has a second wavelength (e.g., 680 nm) near the extreme value of the emission spectrum of the acceptor and a second duration significantly shorter than the FRET lifetime of the acceptor but still long enough such that the filter can effectively block out the second laser pulse from the fluorescence emitted by the acceptor. In this embodiment, the FRET lifetime is about 30 ps and the second duration is set to 1 ps. After the process 600 applies the second pulse, a second FRET process occurs between donors and acceptors in the central small circular area of the focal spot of the first laser pulse. This is the area that the saturation of the first FRET process occurred. At 618, process 600 detects and records the fluorescence emission from the acceptors due to the second FRET process via the third dichroic mirror (e.g., dichroic mirror C 226 of FIG. 2), the filter 228 and PMT 230 by a computing device 202.

After finishing laser scanning one particular location of interest on the trajectory of the sample, process 600 moves to a test 620, in which process 600 determines whether there is another location of interest on the trajectory to be laser scanned. If there are no more locations to be laser scanned, the test 620 is false. The process 600 follows the No-branch to the end. Otherwise, the process 600 follows the Yes-branch to 628 to move the 3D motion stage to the said another location of interest. The process 600 then moves back to 612 to repeat the same process for laser scanning the previous location until the test 620 is false.

The present invention can be implemented in many ways, each of which may yield one or more of the following benefits, advantages or features. One of them is to use a traditional far-field optical microscope to exceed the diffraction-limit resolution. Another advantage is to facilitate the improvement both in lateral and axial resolution within the diffraction-limit resolution simultaneously. Other benefits, advantages or features can be appreciated by those skilled in the art given the detailed description herein.

Although exemplary embodiments of the present invention have been disclosed, it will be apparent to those skilled in the art that various changes and modifications may be made to achieve the advantage of the invention. It will be obvious to those skilled in the art that some components may be substituted with another component providing the same function. The appended claims cover the present invention.

What is claimed is:

1. A method for exceeding diffraction-limit resolution in laser scanning microscopy using fluorescence-resonance-energy-transfer-induced-emission-depletion (FRET-IED), said method comprising:
   preparing a sample by labeling the sample with a plurality of nanoparticles, each of the nanoparticles being co-doped with a controlled ratio of donors and acceptors;
   placing the sample under an objective lens to be laser scanned, wherein the objective lens having an adjustable numerical aperture;
   applying a first laser pulse to form a focal spot of the first laser pulse on a location of interest of the sample with a desired intensity, wherein the focal spot of the first laser pulse is formed by setting the adjustable numerical aperture to highest value in accordance with highest resolution based upon the diffraction-limit;
   applying a second laser pulse to the focal spot of the first laser pulse after a pre-determined time interval; and
   detecting and recording fluorescence emission from the acceptors located within a central small circular area inside the focal spot of the first laser pulse.

2. The method of claim 1, wherein the sample is a live cell.

3. The method of claim 1, wherein the donors and the acceptors are fluorophores, and emission spectrum of the donors and absorption spectrum of the acceptors overlap with each other.

4. The method of claim 1, wherein the nanoparticles are silica nanoparticles.

5. The method of claim 4, wherein the silica nanoparticles have a diameter substantially equal to or less than one-half of the Förster critical distance between one of the donors and one of the acceptors.

6. The method of claim 1, wherein the controlled ratio is preferably five to one for number of donors to number of acceptors, respectively.

7. The method of claim 1, said placing the sample under an objective lens further comprising:
   placing the sample in a three-dimensional motion stage controlled by a computer; and
   traversing a number of said locations of interest of the sample in a trajectory such that a three-dimensional image of the sample can be created.

8. The method of claim 1, wherein the first laser pulse has a first wavelength substantially near peak value of absorption spectrum of the acceptors and a first duration significantly shorter than fluorescence lifetime of the donors.

9. The method of claim 8, wherein the first laser pulse is shot from a first laser source via the first dichroic mirror having high reflection for the first wavelength, and the first dichroic mirror having high transmission for other lights.

10. The method of claim 1, wherein the desired laser intensity has an intensity distribution of Airy pattern with highest value at the center of the focal spot of the first laser pulse.

11. The method of claim 10, wherein the highest value of the desired intensity is configured to achieve saturation of a FRET process between the donors and the acceptors within the central small circular area of the focal spot of the first laser pulse.

12. The method of claim 1, wherein the pre-determined time interval is substantially longer than FRET lifetime of the donors due to excitation of the first laser pulse.

13. The method of claim 1, wherein the second laser pulse has a second wavelength near extreme value in emission spectrum of the acceptors and a second pulse duration significantly shorter than first FRET lifetime of the donors and substantially long such that the second laser pulse and the fluorescence emission from the acceptors are distinguishable by a filter.

14. The method of claim 13, wherein the second laser pulse is shot from a second laser source via a dichroic mirror having high reflection for the second wavelength, and the dichroic mirror having high transmission for the fluorescence emission from the acceptors.

15. The method of claim 1, wherein the adjustable numerical aperture is set to a lower value for the second laser pulse compared to that for the first laser pulse ensuring uniform second laser pulse intensity throughout the focal spot of the first laser pulse.

16. The method of claim 1, said detecting and recording fluorescence emission from the acceptors further comprising:
- setting up a dichroic mirror and a filter having high reflection for the fluorescence emission from the acceptors and high transmission for both the first laser pulse and the second laser pulse; and
- recording the fluorescence emission from the acceptors in a computer via a photomultiple tube.

17. The method of claim 1, wherein the first laser pulse and the second laser pulse are shot from a laser source.

18. A far-field microscope for exceeding diffraction-limit resolution using fluorescence-resonance-energy-transfer-induced-emission-depletion (FRET-IED), said microscope comprising:
- a first laser source providing a first laser pulse for diffraction-limit illumination of a focal spot of the first laser pulse on a location of interest of a sample with a desired intensity, wherein the sample is labeled with a plurality of nanoparticles, each of the nanoparticles being co-doped with a controlled ratio of donors and acceptors;
- a second laser source providing a second laser pulse for uniform illumination of the focal spot of the first laser pulse; and
- a detector for detecting fluorescence emission from the acceptors located within a central small circular area inside the focal spot of the first laser pulse.

19. The microscope of claim 18, further comprising:
- a stage for holding the sample;
- a cover glass on top of the stage;
- an objective lens with adjustable numerical aperture directly located above the cover glass; and
- a computing device controlling the stage and the detector to generate three dimensional image of the sample.

20. The microscope of claim 19, further comprising:
- a first dichroic mirror configuring to facilitate high reflection of the first laser pulse from the first laser source to the sample through the objective lens and the cover glass, and configuring to facilitate high transmission to other lights;
- a second dichroic mirror configuring to facilitate high reflection of the second laser pulse from the second laser source to the sample through the objective lens and the cover glass, and configuring to facilitate high transmission of fluorescence emission from the acceptors and the first laser pulse;
- a third dichroic mirror configuring to facilitate high transmission of the first and the second laser pulses, but high reflection of the fluorescence emission from the acceptors; and
- a filter filtering out the first and the second laser pulses from the fluorescence emission from the acceptors.

21. The microscope of claim 18, wherein the sample is a living cell.

22. The microscope of claim 18, wherein the donors and the acceptors are fluorophores, and emission spectrum of the donors and absorption spectrum of the acceptors overlap with each other.

23. The microscope of claim 18, wherein the nanoparticles are silica nanoparticles.

24. The microscope of claim 23, wherein the silica nanoparticles have a diameter substantially equal to or less than one half of Förster critical distance between one of the donors and one of the acceptors.

25. The microscope of claim 18, wherein the controlled ratio is preferably five to one for number of donors to number of acceptors, respectively.

26. The microscope of claim 25, wherein the three-dimensional motion stage moves in a trajectory controlled by a computing device to generate a three-dimensional image of the sample.

27. The microscope of claim 18, wherein the first laser pulse has a first wavelength substantially near peak value of absorption spectrum of the acceptors and a first duration significantly shorter than FRET lifetime of the donors.

28. The microscope of claim 18, wherein the desired intensity has an intensity distribution of Airy pattern with highest value at the center of the focal spot of the first laser pulse.

29. The microscope of claim 28, wherein the highest value of the desired intensity is configured to achieve saturation of a FRET process between the donors and the acceptors within the central small circular area of the focal spot of the first laser pulse.

30. The microscope of claim 18, wherein the second laser pulse is applied after the first laser pulse after a predetermined time interval, wherein the time interval is substantially longer than FRET lifetime of the donors due to excitation of the first laser pulse.

31. The microscope of claim 18, wherein the second laser pulse has a second wavelength near extreme value in emission spectrum of the acceptors and a second duration significantly shorter than first FRET lifetime of the donors and substantially long such that the second laser pulse and the fluorescence emission from the acceptors are distinguishable by the detector.

32. The microscope of claim 31, wherein the detector is a photomultiple tube.

33. The microscope of claim 18, wherein the fluorescence emission from the acceptors is due to a second FRET after applying both the first laser pulse and the second laser pulse.

34. A far-field microscope for exceeding diffraction-limit resolution using fluorescence-resonance-energy-transfer-induced-emission-depletion (FRET-IED), said microscope comprising:
- a stage for holding a sample labeled with a plurality of nanoparticles, each of the nanoparticles being co-doped with a controlled ratio of donors and acceptors;
- a cover glass on top of the stage;
- an objective lens with adjustable numerical aperture directly located above the cover glass;
- a first laser source providing a first laser pulse;
- a second laser source providing a second laser pulse;
- a first dichroic mirror configuring to facilitate high reflection of the first laser pulse from the first laser source to the sample through the objective lens and the cover glass, and configuring to facilitate high transmission to other lights;
- a second dichroic mirror configuring to facilitate high reflection of the second laser pulse from the second laser source to the sample through the objective lens and the cover glass, and configuring to facilitate high transmission of fluorescence emission from the acceptors and the first laser pulse;
- a third dichroic mirror configuring to facilitate high transmission of the first and the second laser pulses, but high reflection of the fluorescence emission from the acceptors;
- a filter filtering out the first and the second laser pulses from the fluorescence emission from the acceptors;
- a photomultiple tube detecting the fluorescence emission from the acceptors; and
- a computing device controlling the stage and the photomultiple tube to generate three dimensional image of the sample.

* * * * *